(12) United States Patent
Khardekar et al.

(10) Patent No.: US 10,595,965 B2
(45) Date of Patent: Mar. 24, 2020

(54) INTERPROXIMAL REDUCTION PLANNING

(71) Applicant: Align Technology, Inc., San Jose, CA (US)

(72) Inventors: Rahul Khardekar, Sunnyvale, CA (US); Artem Borovinskih, San Jose, CA (US); Rene M. Sterental, Palo Alto, CA (US); Giovanny Garro, La Union (CR); Jason Ramos, San Sebastian (CR); Mitra Derakhshan, Herndon, VA (US); Sergey Kurchatov, Troitsk (RU); Igor Kvasov, Dolgoprudny (RU)

(73) Assignee: Align Technology, Inc., San Jose, CA (US)

(*) Notice: Subject to any disclaimer, the term of this patent is extended or adjusted under 35 U.S.C. 154(b) by 479 days.

(21) Appl. No.: 15/253,148

(22) Filed: Aug. 31, 2016

(65) Prior Publication Data
US 2016/0367339 A1   Dec. 22, 2016

Related U.S. Application Data

(63) Continuation of application No. 13/410,153, filed on Mar. 1, 2012, now Pat. No. 9,433,476.

(51) Int. Cl.
*A61C 7/00* (2006.01)
*G06F 17/50* (2006.01)

(52) U.S. Cl.
CPC .............. *A61C 7/002* (2013.01); *G06F 17/50* (2013.01)

(58) Field of Classification Search
CPC ................................ A61C 7/002; G06F 17/50
(Continued)

(56) References Cited

U.S. PATENT DOCUMENTS 4,134,208 A   1/1979   Pearlman
4,299,568 A   11/1981  Crowley
(Continued)

FOREIGN PATENT DOCUMENTS

CN   1655732 A   8/2005
CN   1655733 A   8/2005
(Continued)

OTHER PUBLICATIONS

Clément Frindel ("Clear thinking about interproximal stripping", Dentofacial Anom Orthod 2010;13:187-199) (Year: 2010).*
(Continued)

*Primary Examiner* — Brian S Cook
*Assistant Examiner* — Iftekhar A Khan
(74) *Attorney, Agent, or Firm* — Shay Glenn LLP (57) ABSTRACT

The present disclosure includes computing device related, systems, and methods for IPR planning as described herein. One method includes identifying a first tooth and a second tooth in a digital dental model with an overlap in a target final position in a treatment plan and identifying a reference line on each of the first tooth and the second tooth; revising the treatment plan wherein a position of each of the first tooth and the second tooth is determined in which the reference line of each of the first tooth and the second tooth are aligned and the first tooth and second tooth are not overlapping; and prescribing IPR based on the determined position of each of the first tooth and the second tooth.

20 Claims, 5 Drawing Sheets

(58) Field of Classification Search
USPC .................................................................. 703/1
See application file for complete search history.

(56) References Cited

U.S. PATENT DOCUMENTS

| | | | |
|---|---|---|---|
| 5,690,486 A | 11/1997 | Zigelbaum | |
| 5,730,151 A | 3/1998 | Summer et al. | |
| 6,183,248 B1* | 2/2001 | Chishti | A61C 7/00 433/6 |
| 6,230,142 B1 | 5/2001 | Benigno et al. | |
| 6,406,292 B1* | 6/2002 | Chishti | A61C 7/00 433/24 |
| 6,976,841 B1 | 12/2005 | Osterwalder | |
| 7,013,191 B2 | 3/2006 | Rubbert et al. | |
| 7,578,673 B2* | 8/2009 | Wen | A61C 7/146 433/24 |
| 7,585,172 B2* | 9/2009 | Rubbert | A61C 7/00 433/24 |
| 7,689,398 B2* | 3/2010 | Cheng | A61C 7/00 433/24 |
| 7,746,339 B2* | 6/2010 | Matov | A61C 19/04 345/419 |
| 7,744,369 B2 | 7/2010 | Imgrund et al. | |
| 8,439,672 B2* | 5/2013 | Matov | A61C 7/00 433/24 |
| 8,465,280 B2 | 6/2013 | Sachdeva et al. | |
| 2002/0010568 A1 | 1/2002 | Rubbert et al. | |
| 2002/0015934 A1 | 2/2002 | Rubbert et al. | |
| 2002/0064746 A1* | 5/2002 | Muhammad | A61C 7/00 433/24 |
| 2004/0029068 A1* | 2/2004 | Sachdeva | A61C 7/00 433/24 |
| 2004/0137400 A1* | 7/2004 | Chishti | A61C 7/00 433/24 |
| 2004/0166463 A1* | 8/2004 | Wen | A61C 7/146 433/24 |
| 2004/0197727 A1* | 10/2004 | Sachdeva | A61C 7/00 433/24 |
| 2004/0229185 A1 | 11/2004 | Knopp | |
| 2005/0271996 A1* | 12/2005 | Sporbert | A61C 7/00 433/24 |
| 2006/0194163 A1* | 8/2006 | Tricca | A61C 7/00 433/24 |
| 2006/0275731 A1 | 12/2006 | Wen et al. | |
| 2006/0275736 A1* | 12/2006 | Wen | A61C 9/00 433/213 |
| 2007/0263226 A1 | 11/2007 | Kurtz et al. | |
| 2008/0057461 A1* | 3/2008 | Cheng | A61C 7/00 433/24 |
| 2008/0062429 A1 | 3/2008 | Liang et al. | |
| 2008/0118886 A1 | 5/2008 | Liang et al. | |
| 2008/0169122 A1 | 7/2008 | Shiraishi et al. | |
| 2009/0029310 A1* | 1/2009 | Pumphrey | A61C 7/08 433/24 |
| 2009/0087050 A1 | 4/2009 | Gandyra | |
| 2009/0105523 A1 | 4/2009 | Kassayan et al. | |
| 2009/0130620 A1 | 5/2009 | Yazdi et al. | |
| 2009/0170050 A1 | 7/2009 | Marcus | |
| 2009/0281433 A1 | 11/2009 | Saadat et al. | |
| 2009/0286195 A1 | 11/2009 | Sears et al. | |
| 2009/0286196 A1* | 11/2009 | Wen | A61C 7/00 433/24 |
| 2009/0317757 A1 | 12/2009 | Lemchen | |
| 2010/0015565 A1 | 1/2010 | Carrillo Gonzalez et al. | |
| 2010/0280798 A1* | 11/2010 | Pattijn | A61C 7/002 703/1 |
| 2011/0065060 A1 | 3/2011 | Teixeira et al. | |
| 2011/0136090 A1 | 6/2011 | Kazemi | |
| 2011/0143300 A1 | 6/2011 | Villaalba | |
| 2012/0064477 A1 | 3/2012 | Schmitt | |
| 2012/0150494 A1* | 6/2012 | Anderson | A61C 7/002 703/1 |
| 2013/0089828 A1* | 4/2013 | Borovinskih | A61C 7/08 433/6 |
| 2013/0204599 A1* | 8/2013 | Matov | G16H 50/50 703/11 |
| 2013/0209952 A1* | 8/2013 | Kuo | A61C 7/002 433/10 |
| 2013/0317800 A1* | 11/2013 | Wu | A61C 7/002 703/11 |
| 2013/0325431 A1* | 12/2013 | See | G16B 5/00 703/11 |
| 2014/0178829 A1 | 6/2014 | Kim | |
| 2014/0186794 A1 | 7/2014 | Deichmann et al. | |
| 2015/0216627 A1* | 8/2015 | Kopelman | A61C 7/08 433/6 |
| 2015/0366637 A1* | 12/2015 | Kopelman | A61C 7/08 433/6 |
| 2016/0175068 A1* | 6/2016 | Cai | A61C 7/002 700/98 |
| 2016/0287358 A1 | 10/2016 | Nowak et al. | |
| 2016/0310236 A1* | 10/2016 | Kopelman | A61C 7/002 |
| 2017/0007365 A1* | 1/2017 | Kopelman | A61C 7/08 |
| 2017/0007386 A1* | 1/2017 | Mason | B44C 1/28 |
| 2017/0008333 A1* | 1/2017 | Mason | B44C 1/28 |
| 2019/0175303 A1* | 6/2019 | Akopov | A61C 7/002 |

FOREIGN PATENT DOCUMENTS

| | | |
|---|---|---|
| CN | 103889364 A | 6/2014 |
| JP | 2007537824 A | 12/2007 |
| JP | 2008067732 A | 3/2008 |
| JP | 2012045143 A | 3/2012 |
| WO | WO2012/078980 A2 | 6/2012 |

OTHER PUBLICATIONS

Livas et al. ("Enamel Reduction Techniques in Orthodontics: A Literature Review", The Open Dentistry Journal, 2013, 7, 146-151) (Year: 2013).*

3 Shape Trios 3; Insane speed-scanning with 3shape trios 3 intracral canner; (Screenshot); 2 pages; retrieved from the internet at You Tube (https//www.youtube.com/watch?v=X5CviUZ5DpQ&feature=youtu.be; available as of Sep. 18, 2015.

Dentalwings; I series dental impression scanner; 8 pages; retrieved from the internet (https://web.archive.org/web/20160502145908/http://www.dentalwings.com/products/scan-and-design-systems/iseries/); available as of May 2, 2016.

Dentalwings; Intraoral scanner; 7 pages; retrieved from the internet (https://web.archive.org/web/20160422114335/http://www.dentalwings.com/products/intraoral-scanner/); available as of Apr. 4, 2016.

Video of DICOM to Surgical Guides; Can be viewed at <URL:https://youtu.be/47KtOmCEFQk; Published Apr. 4, 2016.

* cited by examiner

INTERPROXIMAL REDUCTION PLANNING

PRIORITY INFORMATION

The present application is a continuation of U.S. patent application Ser. No. 13/410,153, filed on Mar. 1, 2012, the contents of which are incorporated herein by reference.

BACKGROUND

The present disclosure is related generally to the field of dental treatment. More particularly, the present disclosure relates to interproximal reduction planning.

Many dental treatments involve repositioning misaligned teeth and changing bite configurations for improved cosmetic appearance and dental function. Orthodontic repositioning can be accomplished, for example, through a dental process that uses one or more removable positioning appliances for realigning teeth.

Such appliances may utilize a shell of material having resilient properties, referred to as an "aligner" that generally conforms to a patient's teeth but is slightly out of alignment with the initial tooth configuration. Placement of an appliance over the teeth can provide controlled forces in specific locations to gradually move the teeth into a new configuration. Repetition of this process with successive appliances in progressive configurations can move the teeth through a series of intermediate arrangements to a final desired arrangement.

Repositioning a patient's teeth may result in residual crowding of adjacent teeth due to insufficient space within the patient's mouth. This residual crowding can impede complete tooth alignment. In some situations it may be possible to remove a small portion of a tooth, or portions of two adjacent teeth, in order to make the teeth fit within the space available. The removal of material causing the overlap of the crowded teeth must be treated by the treatment professional by removing material from the surface of one or more teeth in a process called interproximal reduction (IPR). During an IPR procedure, a small amount of enamel thickness on the surface of the teeth is removed to reduce the mesial-distal width and space requirements for the tooth.

One problem experienced during dental treatment is the determination by the treatment professional of whether an IPR procedure is necessary and the timing of IPR within the treatment. If the IPR procedure is conducted in a stage of the treatment that is too early or too late, the treatment professional may have poor access to the surfaces of the one or more teeth intended to be removed. Further, the treatment professional may inaccurately remove material from the surface of the tooth resulting in an undesired tooth shape, a tooth surface that does not fit properly against another tooth, and potentially having to perform additional IPR procedures and/or other procedures to fix the overlap or newly created underlap.

DETAILED DESCRIPTION

Embodiments of the present disclosure include computing device related, system, and method embodiments for interproximal reduction planning. For example, one or more embodiments include a computing device implemented method that includes identifying a first tooth and a second tooth in a digital dental model with an overlap in a target position in a treatment plan, identifying a reference line on each of the first tooth and the second tooth, revising the treatment plan wherein a position of each of the first tooth and the second tooth is determined in which the reference line of the first tooth and the reference line of the second tooth are aligned and the first tooth and the second tooth are not overlapping, and prescribing interproximal reduction based on the determined position of each of the first tooth and the second tooth.

In the following detailed description of the present disclosure, reference is made to the accompanying drawings that form a part hereof, and in which is shown by way of illustration how a number of embodiments of the disclosure may be practiced. These embodiments are described in sufficient detail to enable those of ordinary skill in the art to practice a number of embodiments of this disclosure, and it is to be understood that other embodiments may be utilized and that changes may be made without departing from the scope of the present disclosure.

As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate the embodiments of the present disclosure, and should not be taken in a limiting sense. As used herein, "a", "at least one", "a number of" something can refer to one or more such things.

Although the overarching term "orthodontics" is used herein, the present disclosure may relate to treatments of an orthognathic nature. For example, in cases including treatment of a patient's underlying skeletal structure, teeth may be rearranged by surgically repositioning underlying bones that hold the teeth in order to achieve a desired final bite arrangement. In both orthodontic and orthognathic treatment approaches, alignment of the teeth may be evaluated pre-, mid-, and/or post-treatment.

Treatment professionals, such as a clinician, typically select a treatment plan for a patient's teeth based upon experience with certain types of physical features and/or appliances. In some embodiments, a dental treatment plan can include orthodontic treatment planning functions and/or appliances. IPR procedures are often left to be done at the end of a dental treatment, however, there may not be enough space to properly align the teeth at this point in the treatment.

IPR planning within a dental treatment plan can be beneficial, for example, in that planning for IPR can consider the ease of performing IPR. The planning of IPR can result in more accurate access to the IPR regions as compared to non-planning for IPR, more accurate removal of the IPR regions as compared to non-planning for IPR, and the elimination of additional procedures to fix errors caused by inaccurate IPR timing, among other benefits.

In various embodiments, with the use of computer device executable instructions, a treatment professional can establish a treatment plan having a target position for a number of teeth of a particular patient. With this target position in mind, a first tooth and a second tooth needing IPR can be identified and IPR can be virtually planned at a point during the process of moving the teeth to the target position that is desirable for performing IPR.

Digital dental models from a scan of a patient's dentition can be provided with computer-aided design and/or manufacturing systems, including tooth-treatment systems. A digital dental model representing an initial tooth arrangement may be obtained in a variety of ways.

For example, the patient's teeth may be imaged to obtain digital data using direct and/or indirect structured light, X-rays, three-dimensional X-rays, lasers, destructive scanning, computer-aided tomographic images or data sets, magnetic resonance images, intra-oral scanning technology, photographic reconstruction, and/or other imaging techniques. The digital dental model can include an entire mouth tooth arrangement, some, but not all teeth in the mouth, and/or it can include a single tooth.

A positive model and/or negative impression of the patient's teeth or a tooth may be scanned using an X-ray, laser scanner, destructive scanner, structured light, and/or other range acquisition system to produce the initial digital dental model. The data set produced by the range acquisition system may be converted to other formats to be compatible with the software which is used for manipulating images within the data set, as described herein.

Figure 1A:
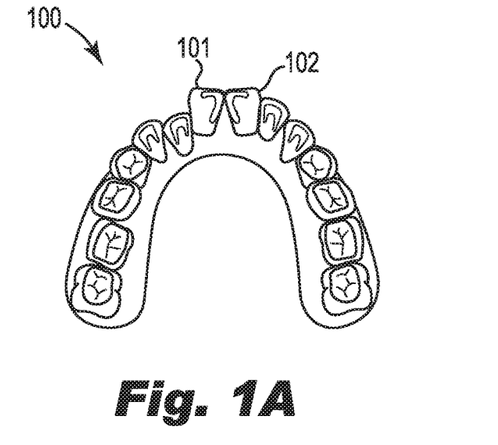
FIG. 1A illustrates an example of a digital dental model according to one or more embodiments of the present disclosure.
Figure 1B:
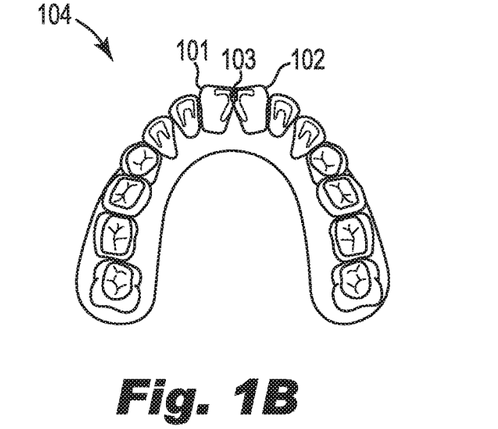
FIG. 1B illustrates an example of a target digital dental model according to one or more embodiments of the present disclosure.

Referring now to FIG. 1A, there is illustrated an example of a digital dental model 100 according to one or more embodiments of the present disclosure. As described herein, the digital dental model 100 can be obtained prior to treatment or at an intermediate state of treatment (e.g., before treatment has been completed). The digital dental model 100 can include an initial position of a first tooth 101 and a second tooth 102 or a number of teeth. FIG. 1B illustrates a target digital dental model 104 according to one or more embodiments of the present disclosure. The target digital dental model 104 can be created by modifying the digital dental model 100 according to one or more treatment goals. The target digital dental model 104 can include a target position in a treatment plan of a first tooth 101 and a second tooth 102 and a target position of a number of teeth, for example. The one or more treatment goals can be case-specific (e.g., specific to the particular patient on which the digital dental model 100 was based).

In some embodiments, a first tooth 101 and a second tooth 102 can be identified in the digital dental model 100 with an overlap 103 in a target position in a treatment plan. An overlap 103 can include an overlap with a neighboring tooth 102 along an arch of the target digital dental model 104 and a potential collision in the target position with a neighboring tooth 102, among many others. An overlap 103 that can be remedied through IPR can be approximately 0.50 millimeters, for example. For instance, in such an example, approximately 0.25 millimeters of the first tooth 101 and 0.25 millimeters of the second tooth 102 can be removed via an IPR procedure. In some IPR procedures, the amount of tooth material removed can be different for two adjacent teeth (e.g., 0.25 mm and 0.15 mm).

Figure 1C:
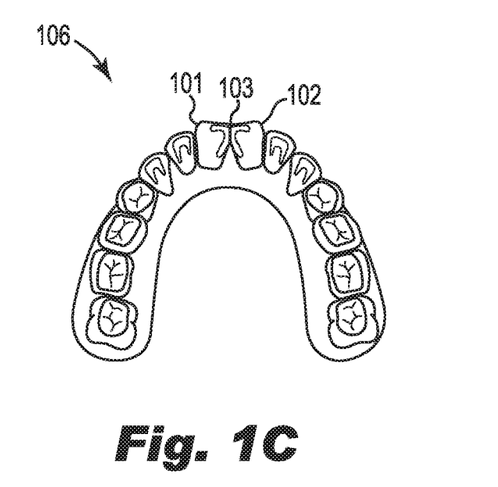
FIG. 1C illustrates an example of a revised target digital dental model according to one or more embodiments of the present disclosure.

FIG. 10 illustrates a revised target digital dental model 106 after IPR prescription according to one or more embodiments of the present disclosure. The revised target digital dental model 106 can be created by modifying the digital dental model 100 and the target digital dental model 104 according to the IPR prescribed at the determined position.

For example, the revised target digital dental model 106 can include a digital removal of the portion of the first tooth 101 and second tooth 102 overlapping 103 in the target digital dental model 104 and identified to be removed at the determined position. In some embodiments, the removed portion 103 can include a total of approximately 0.25 millimeters of the first tooth 101 and 0.25 millimeters of the second tooth 102 for a total removed portion 103 of approximately 0.50 millimeters, for example. Such an amount of removal can be beneficial for the cosmetic appearance and/or the structural integrity of the teeth 101, 102 prescribed for IPR.

In various embodiments of the present disclosure, the treatment plan can include a plurality of stages. For example, at a determined position of the revised treatment plan a number of additional stages can be inserted into the revised treatment plan.

A first additional stage can include removing an overlap of the first tooth 101 and the second tooth 102. For example, the first additional stage can include expanding the arch of the first tooth 101 and the second tooth 102. The expansion can include digitally changing a mesial position or distal position of at least one tooth of the first tooth 101 and the second tooth 102, among others. A second additional stage can include aligning the first tooth 101 and the second tooth 102 for IPR.

In various embodiments, the process can include reclining the first tooth 101 and the second tooth 102 to a revised target position in the revised target digital dental model 106 after IPR prescription. In various embodiments, a number of teeth without overlap can be reclined to a revised target position in the revised target digital dental model 106 after IPR prescription.

In some embodiments, the target digital dental model 104 and revised target digital dental model 106 can reflect an intermediate tooth movement within a treatment plan. Such a tooth movement may be useful during a particular process within the treatment plan (e.g., IPR, extraction, etc.).

In some embodiments, the digital dental model 100, target digital dental model 104, and the revised target digital dental model 106 can be displayed via a user interface in three dimensions.

Figure 2A:
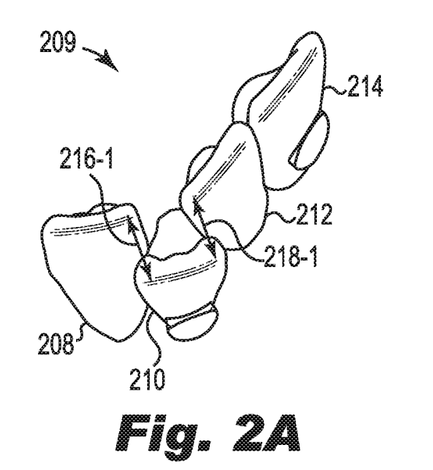
FIGS. 2A-2B illustrate examples of a ridge endpoint reference line on each of a first tooth and a second tooth according to one or more embodiments of the present disclosure.
Figure 2B:
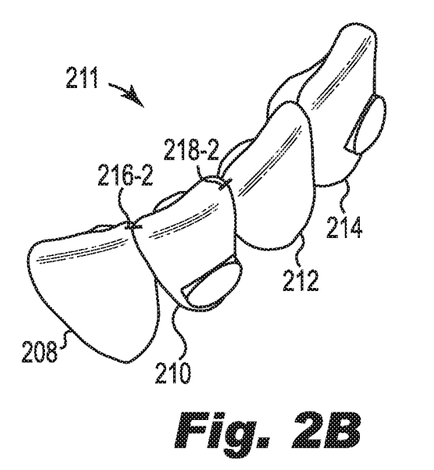
Figure 2C:
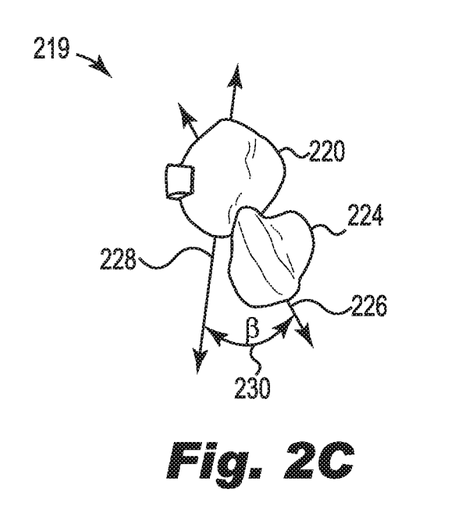
FIG. 2C illustrates an example of a y-axis reference line on each of a first tooth and a second tooth according to one or more embodiments of the present disclosure.

FIGS. 2A-2C illustrate examples of a reference line on each of a first tooth and a second tooth. In various embodiments of the present disclosure, a reference line on each of the first tooth and the second tooth can be identified.

FIGS. 2A-2B illustrate examples of a ridge endpoint reference line 216-1, 216-2, 218-1, 218-2 on each of a first tooth 208 and a second tooth 210 according to one or more embodiments of the present disclosure. The first tooth 208 and the second tooth 210 can be among a number of teeth 208, 210, 212, and 214 in a treatment plan.

In one or more embodiments, a reference line can be identified on each of the first tooth 208 and the second tooth 210 by calculating the distance difference between ridge endpoints of each of the first tooth 208 and the second tooth 210 at the determined position 209 of each tooth and at the target position 211 of each tooth. For example, the distance 216-1 between the ridge endpoints of the first tooth 208 and the second tooth 210 at the determined position 209 and the distance 216-2 at the target position 211 can be measured. The distance 216-1 at the determined position 209 minus the distance 216-2 at the target position 211 can then be calculated.

In various embodiments of the present disclosure, the reference lines of the first tooth 208 and the second tooth 210 may be aligned if the distance difference between the ridge endpoints at the determined position 209 and the target position 211 is within a threshold difference. The threshold distance difference can be a distance that is predetermined (e.g., by a treatment professional). For example, a threshold distance difference can be a distance of 0.75 millimeters.

Such a threshold may indicate that the teeth are aligned vertically and/or laterally such that IPR can be performed. For instance, a distance difference threshold of 0.75 millimeters may result in the identification and alignment of teeth that may be severely misaligned for IPR if IPR is left to be performed at the end of the dental treatment. Teeth severely misaligned for IPR can include teeth that would be difficult or impossible for a treatment professional to perform an IPR procedure on at the end of the dental treatment.

FIG. 2C illustrates an example 219 of a y-axis reference line 228, 226 on each of a first tooth 220 and a second tooth 224 according to one or more embodiments of the present disclosure. In one or more embodiments, a reference line 228, 226 can be identified on each of a first tooth 220 and a second tooth 224 by calculating the y-axis of the first tooth 228 and the y-axis of the second tooth 226. For example, the y-axis of the first tooth 228 and the second tooth 226 can include the mesial-distal local axis of a tooth.

In various embodiments of the present disclosure, the y-axis reference lines 228, 226 of the first tooth 220 and the second tooth 224 may be aligned if the angle 230 between the y-axis of the first tooth 228 and the y-axis of the second tooth 226 is within a threshold angle β. The threshold angle β can be an angle that is predetermined (e.g., by a treatment professional). For example, the threshold angle β may be 20 degrees. Such a threshold may indicate that the teeth are aligned vertically and/or laterally such that IPR can be performed.

In various embodiments of the present disclosure, the reference lines of the first tooth 220 and the second tooth 224 may be aligned if the angle 230 between the y-axis of the first tooth 228 and the y-axis of the second tooth 226 at a target position is greater than the angle 230 of the y-axis of the first tooth 228 and the y-axis of the second tooth 226 at the determined position. For example, if the angle 230 at the target position is approximately 30 degrees and the angle 230 at the determined position is approximately 25 degrees, then the first tooth 220 and the second tooth 226 may be aligned for IPR at the determined position. A greater y-axis angle at the target position may indicate that the teeth are aligned vertically and/or laterally such that IPR can be performed.

In some embodiments of the present disclosure, the reference lines of the first tooth and second tooth may be aligned if the calculated difference between the ridge endpoints of the first tooth and the second tooth at the determined position and the target position is within a threshold distance, if the angle between the first tooth and the second tooth at the determined position is within a threshold angle, or if the calculated angle between the y-axis of the first tooth and the second tooth at the target position is greater than the calculated angle at the determined position, or any combination thereof. The combination may indicate that the teeth are aligned vertically and/or laterally such that IPR can be performed. For example, the combination may result in more accurate identification and alignment of teeth that may be severely misaligned for an IPR procedure if IPR is left to be performed at the end of the dental treatment.

Figure 3:
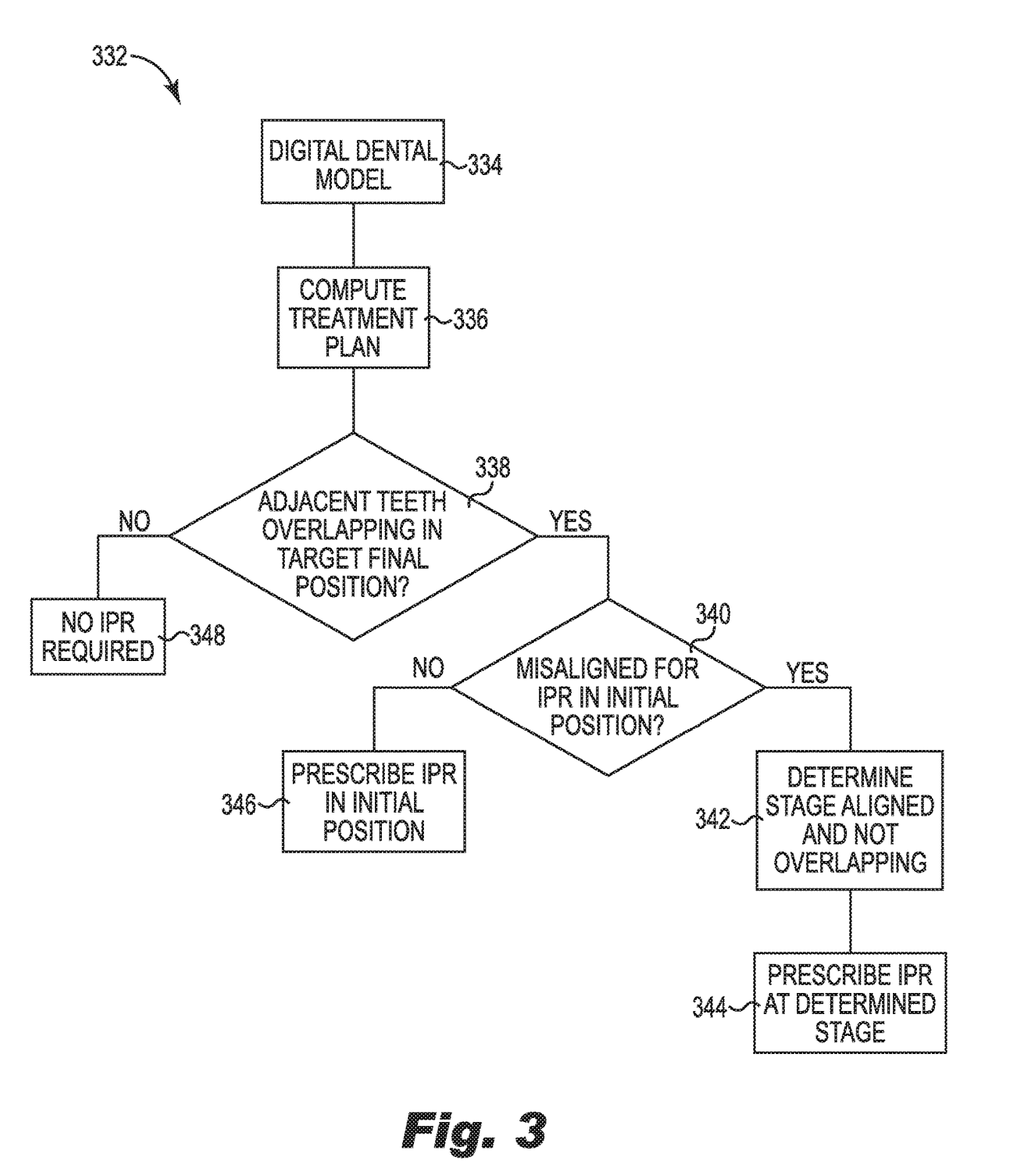
FIG. 3 is a flow chart illustrating an example of a process for IPR planning according to one or more embodiments of the present disclosure.

FIG. 3 is a flow chart illustrating an example of a process 332 for IPR planning according to one or more embodiments of the present disclosure. At 334, a digital dental model can be created from data received. For example, a digital dental model can be created from a scan of a patient's dentition and provided with computer-aided design and/or manufacturing systems, including tooth-treatment systems.

The digital dental model can include data for a number of teeth. The digital dental model can include an initial digital dental model or an intermediate position of a digital dental model, for example.

At 336, a treatment plan can be computed from the digital dental model. The treatment plan can include moving a number of teeth to a target position of the treatment plan. In various embodiments of the present disclosure, the treatment plan can include a plurality of stages.

At 338, a determination can be made as to whether a first tooth overlaps with a second tooth in the target position. A first tooth overlapping with a second tooth can include a potential collision in the target position with a neighboring tooth. In various embodiments of the present disclosure, the first tooth that overlaps with the second tooth can be overlapping with a number of teeth on different sides of the first tooth.

In response to no identified overlapping teeth in the target position, at 348, the process 332 can identify that IPR planning may not be required.

In response to determining that a first tooth overlaps with a second tooth, at 340, a determination can be made as to whether the first tooth and the second tooth are misaligned for IPR in the initial position. Misalignment in the initial position can include no access for a treatment professional to perform IPR. For example, the distance between the IPR region of the first tooth and the IPR region of the second tooth may be too small for a treatment professional to perform IPR.

In response to a determination that the teeth are not misaligned for IPR in the initial position, at 346, IPR can be prescribed in the initial position. In response to a determination that the teeth are misaligned for IPR in the initial position, the treatment plan can be revised. At 342, a stage can be identified or a stage can be added in the treatment plan wherein the reference line of the first tooth and the reference line of the second tooth are aligned and the teeth are not colliding. At 344, IPR can be prescribed on the first tooth and the second tooth at the identified or added stage.

Figure 4:
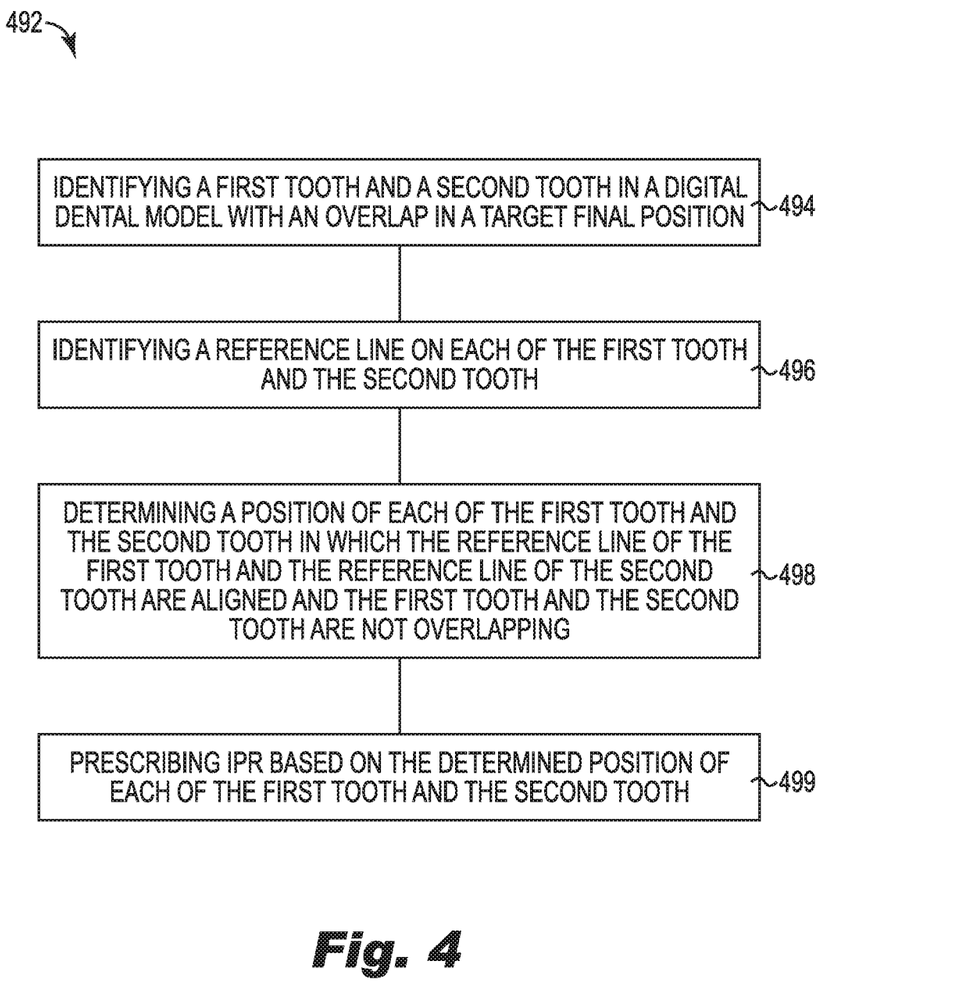
FIG. 4 illustrates an example of a method for IPR planning according to one or more embodiments of the present disclosure.

FIG. 4 illustrates an example of a method 492 for IPR planning according to one or more embodiments of the present disclosure. At 494, a first tooth and a second tooth with an overlap in a target position of a treatment plan can be identified in a digital dental model. For example, an overlap can include a calculated overlap or a potential collision in a target position with a neighboring tooth.

In various embodiments of the present disclosure, an overlap between a first tooth and a second tooth can be disregarded wherein the first tooth and the second tooth are at least one of a molar and/or a premolar. Disregarding molars and/or premolars can include not aligning the identified overlapping molars and/or premolars for IPR and not planning IPR for the overlapping molars and/or premolars. For example, an overlapping molar and/or premolar can include an overlap between a first molar and a second molar, an overlap between a first molar and a first premolar, and an overlap between a first premolar and a second premolar.

At 496, a reference line can be identified for each of the first tooth and the second tooth. In various embodiments, a reference line can include a distance between the ridge endpoints of each of the first tooth and the second tooth. In various embodiments, a reference line can include a y-axis of each of the first tooth and the second tooth. A y-axis of each tooth can include a mesial-distal local axis of the tooth, for example.

A reference line between the ridge endpoints of each of a first tooth and a second tooth can be used on teeth with well defined ridges in various embodiments of the present disclosure. For example, a ridge endpoint reference line may be determined on incisor and/or canine teeth, and a ridge endpoint reference line may not be suitable on molar and/or premolar teeth.

At 498, a position of each of the first tooth and the second tooth is determined in which the reference line of the first tooth and the reference line of the second tooth are aligned and not overlapping.

At 499, IPR can be prescribed based on the determined position of each of the first tooth and the second tooth. For example, IPR prescription can include indicating in a treatment plan that an IPR procedure is to be done at a particular stage of the plan based on this analysis.

Figure 5:
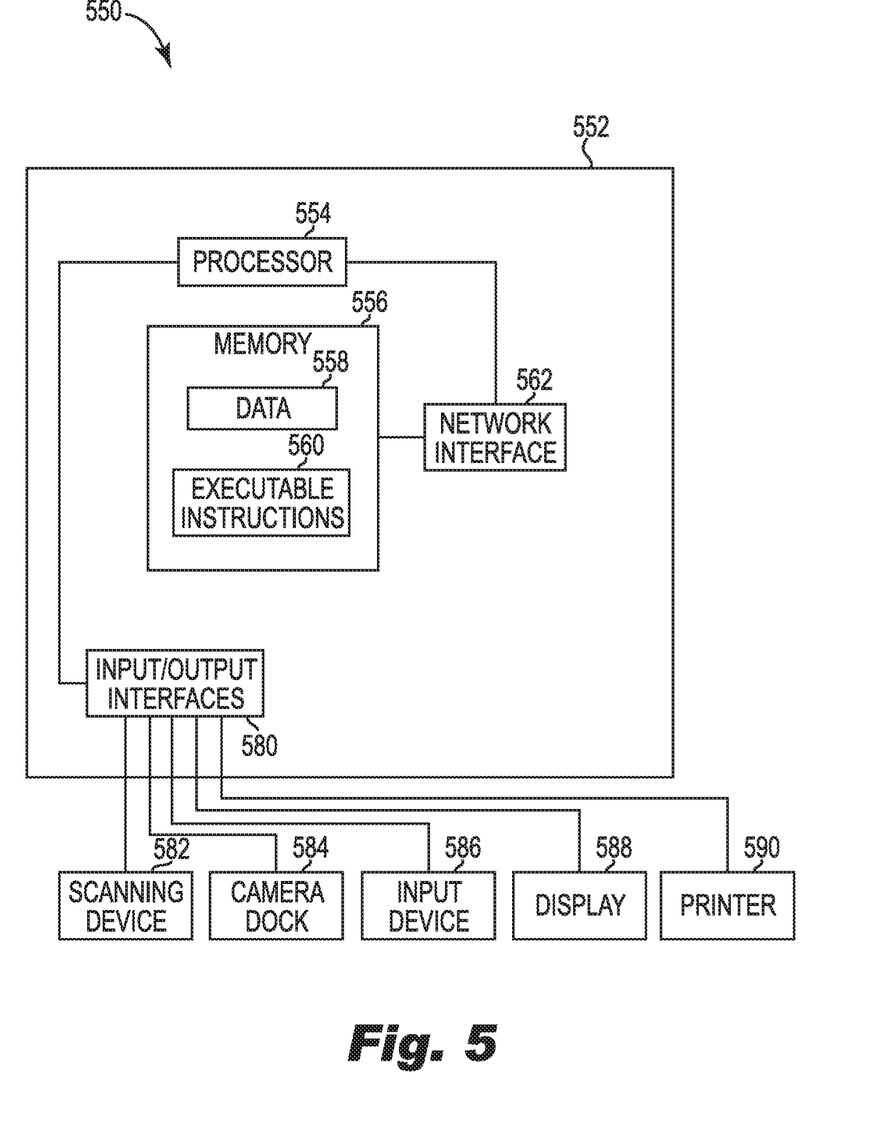
FIG. 5 illustrates an example of a system for IPR planning according to one or more embodiments of the present disclosure.

FIG. 5 illustrates an example of a system 550 for IPR planning according to one or more embodiments of the present disclosure. In the system 550 in FIG. 5, the system 550 includes a computing device 552 having a number of components coupled thereto. The computing device 552 includes a processor 554 and a memory 556. The memory 556 can have various types of information including data 558 and executable instructions 560, as discussed herein.

The processor 554 can execute instructions 560 that are stored on an internal or external non-transitory computer device readable medium (CRM). A non-transitory CRM, as used herein, can include volatile and/or non-volatile memory. Volatile memory can include memory that depends upon power to store information, such as various types of dynamic random access memory (DRAM), among others. Non-volatile memory can include memory that does not depend upon power to store information.

Memory 556 and/or the processor 554 may be located on the computing device 552 or off the computing device 552, in some embodiments. As such, as illustrated in the embodiment of FIG. 5, a system 550 can include a network interface 562. Such an interface 562 can allow for processing on another networked computing device, can be used to obtain information about the patient, and/or can be used to obtain data and/or executable instructions for use with various embodiments provided herein.

As illustrated in the embodiment of FIG. 5, a system 550 can include one or more input and/or output interfaces 580. Such interfaces 580 can be used to connect the computing device 552 with one or more input and/or output devices 582, 584, 586, 588, and 590.

For example, in the embodiments illustrated in FIG. 5, the system 550 can include connectivity to a scanning device 582, a camera dock 584, an input device 586 (e.g. a mouse, a keyboard, etc.), a display device 588 (e.g., a monitor), a printer 590, and/or one or more other input devices. The input/output interface 580 can receive executable instructions and/or data, storable in the data storage device (e.g., memory 556), representing a digital dental model, target digital dental model, and/or a revised target digital dental model of a patient's dentition.

In some embodiments, the scanning device 582 can be configured to scan one or more physical molds of a patient's dentition. In one or more embodiments, the scanning device 582 can be configured to scan the patient's dentition directly. The scanning device 582 can be configured to input data into the computing device 552.

In some embodiments, the camera dock 584 can receive an input from an imaging device (e.g., a two-dimensional or three-dimensional imaging device) such as a digital camera, a printed photograph scanner, or other suitable imaging device. The input from the imaging device can, for example, be stored in memory 556.

The processor 554 can execute instructions to provide a visual indication of a treatment plan and/or provided stage for IPR planning on the display 588. The computing device 550 can be configured to allow a treatment professional or other user to input treatment goals. Input received can be sent to the processor 554 as data and/or can be stored in memory 556.

Such connectivity can allow for the input and/or output of data and/or instructions among other types of information. Although some embodiments may be distributed among various computing devices within one or more networks, such systems as illustrated in FIG. 5, can be beneficial in allowing for the capture, calculation, and/or analysis of information discussed herein.

The processor 554, in association with the data storage device (e.g., memory 556), can be associated with data 558. The processor 454, in association with the memory 456, can store and/or utilize data 558 and/or execute instructions 560 for IPR planning. Such data 558 can include the digital dental model, target digital dental model, and/or the revised target digital dental model.

The processor 554 coupled to the memory 556 can analyze a target digital dental model of a treatment plan, including tooth data for a number of teeth, to identify if a first tooth in the number of teeth overlaps with a neighboring tooth along an arch of the target digital dental model. The overlap can include a collision of a first tooth and a second tooth in a target position within a target digital dental model, for example.

The processor 554 coupled to the memory 556 can revise the treatment plan to remove the overlap and align the first tooth and neighboring tooth for IPR, prescribe IPR on the first tooth and the neighboring tooth in the aligned position, and recline the first tooth and the neighboring tooth to a revised target position in a revised target digital dental model after IPR prescription. Removing the overlap can include expanding the arch by digitally changing a mesial position or a distal position of at least one tooth of the first tooth and the neighboring tooth, among many others. Prescription of IPR can include a notification of the aligned position and a digital representation of the region of the first tooth and the second tooth removed by the IPR procedure prescribed, for example.

In various embodiments of the present disclosure, the processor 554 coupled to the memory 556 can recline a number of teeth without undesired overlap in the digital dental model to the revised target position in the revised target digital dental model after IPR prescription.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

The invention claimed is:

1. A computing device implemented method for interproximal reduction (IPR) planning, comprising:
   identifying a first ridge endpoint reference line between a ridge endpoint of a first tooth and a ridge endpoint of a second tooth, wherein the first tooth and the second tooth are adjacent and overlap at a target position of the first tooth and the second tooth during treatment plan, wherein the first tooth and the second tooth are of a number of teeth included in a digital dental model of the treatment plan;
   identifying a second ridge endpoint reference line between the ridge endpoint of the first tooth and the ridge endpoint of the second tooth at a provided stage of the treatment plan, wherein the first and second endpoint reference lines are along a mesial-distal local axis of the first tooth and the second tooth;
   calculating a distance difference between the first and second ridge endpoint reference lines; and
   revising the treatment plan to provide an intermediate position for the first tooth and the second tooth within the treatment plan in response to an identification that the first tooth overlaps with the second tooth, wherein:
      revising the treatment plan includes removing an overlap of the first tooth and the second tooth in the digital dental model such that the first tooth and the second tooth are aligned sufficiently for IPR to be performed based on the calculated distance difference between the first and second ridge endpoint reference lines being within a specified threshold distance; and
      the first tooth and the second tooth are not overlapping such that IPR can be performed on at least one of the first tooth and the second tooth.

2. The method of claim 1, including determining the intermediate position of the first tooth and the second tooth by calculating a distance difference between a first ridge endpoint of the first tooth and a second ridge endpoint of the second tooth at the intermediate position and at the target position.

3. The method of claim 2, wherein the first ridge endpoint and the second ridge endpoint are aligned when the calculated distance difference between the first ridge endpoint and the second ridge endpoint at the intermediate position and at the target position are within a threshold distance.

4. The method of claim 1, including determining the intermediate position of each of the first tooth and the second tooth based on the calculated distance difference between the ridge endpoint reference line and the second ridge endpoint reference line at the intermediate position of each of the first tooth and the second tooth.

5. The method of claim 4, wherein the first tooth and the second tooth are aligned if the calculated distance between the ridge endpoint reference line of the first tooth and the second tooth at the intermediate position is within a threshold distance.

6. The method of claim 1, including determining the intermediate position of each of the first tooth and the second tooth based on a calculated distance between a ridge endpoint reference line of the first tooth and the second tooth at the intermediate position and at the target position.

7. The method of claim 6, wherein the first tooth and the second tooth are aligned when the calculated distance at the target position is greater than the calculated distance at the intermediate position.

8. The method of claim 1, wherein the method further includes disregarding an overlap between a first molar and a second molar or between an premolar and a molar.

9. A system for interproximal reduction (IPR) planning, comprising:
   a processor; and
   a memory coupled to the processor and configured to direct the processor to:
      identify when a first tooth of a number of teeth overlaps with a neighboring tooth of the number of teeth representing one dental arch of a patient, wherein the number of teeth are included in a target digital dental model of a treatment plan;
      calculate a distance between a mesial-distal reference line of the first tooth and a mesial-distal reference line of the neighboring tooth at a provided stage of the treatment plan; and
      in response to an identification that the first tooth overlaps with the neighboring tooth of the target digital dental model, revise the treatment plan to:
         remove the overlap and align the first tooth and the neighboring tooth in an intermediate position within the treatment plan in which the mesial-distal reference line of the first tooth and the mesial-distal reference line of the neighboring tooth are aligned sufficiently for IPR to be performed on at least one of the first and neighboring tooth based on the calculated distance between the mesial-distal reference line of the first tooth and the mesial-distal reference line of the neighboring tooth being within a specified threshold;
         prescribe IPR on the first tooth and the neighboring tooth in the intermediate position; and
         recline the first tooth and the neighboring tooth to a revised target position in a revised target digital dental model after IPR prescription.

10. The system of claim 9, wherein the memory further directs the processor to identify the first tooth in the number of teeth that overlaps with a number of neighboring teeth on different sides of the first tooth.

11. The system of claim 9, wherein the memory further directs the processor to a change a mesial position of at least one tooth of the first tooth and the neighboring tooth to remove the overlap of the teeth.

12. The system of claim 9, wherein the memory further directs the processor to change a distal position of at least one tooth of the first tooth and the neighboring tooth to remove the overlap of the teeth.

13. The system of claim 9, wherein the memory further directs the processor to recline a number of teeth without undesired overlap in the target digital dental model to a revised target position in the revised target digital dental model after IPR prescription.

14. A non-transitory computing device readable medium having executable instructions that can be executed by a processor to cause a computing device to perform a method for interproximal reduction (IPR) planning, comprising:
   computing a treatment plan for moving a number of teeth within a set of teeth representing one dental arch of a patient to a target position;
   identifying a first tooth in the number of teeth having a potential collision in the target position with a neighboring tooth;
   detecting misalignment for IPR of the first tooth and the neighboring tooth in an initial position of the first tooth and the neighboring tooth;
   calculating a distance between a mesial-distal reference line of the first tooth and a mesial-distal reference line of the neighboring tooth at a provided stage of the treatment plan;
   revising the treatment plan to:
      provide a stage including an intermediate position within the treatment plan of the first tooth and the neighboring tooth in which the mesial-distal reference line of the first tooth and the mesial-distal reference line of the neighboring tooth are aligned sufficiently for IPR to be performed on at least one of the first and neighboring tooth, wherein the first tooth and the neighboring tooth do not collide based on the calculated distance between the mesial-distal reference line of the first tooth and the mesial-distal reference line of the neighboring tooth being within a specified threshold; and
      prescribing IPR on the first tooth and the neighboring tooth at the provided stage.

15. The non-transitory computing device readable medium of claim 14, wherein the mesial-distal reference lines are aligned if the calculated distance is approximately 0.75 millimeters or less.

16. The non-transitory computing device readable medium of claim 14, wherein the instructions can further be executed to perform the method including providing the stage of the treatment plan by computing an angle between a ridge of the first tooth and a ridge of the neighboring tooth at the provided stage and at the target position, wherein the mesial-distal reference lines are aligned when the calculated angle is approximately 20 degrees or less.

17. The non-transitory computing device readable medium of claim 14, wherein the instructions can further be executed to perform the method including providing the stage of the treatment plan by computing difference of an angle between the mesial-distal reference line of the first tooth and the mesial-distal reference line of the neighboring tooth at the provided stage and an angle between the mesial-distal reference line of the first tooth and the mesial-distal reference line of the neighboring tooth at the target position.

18. The non-transitory computing device readable medium of claim 14, wherein the instructions can be executed to compute a plurality of stages in the treatment plan.

19. The non-transitory computing device readable medium of claim 18, wherein the instructions can be executed to insert a number of sub-stages at the provided stage of the treatment plan, wherein a first sub-stage of the number of sub-stages includes expanding the arch of the first tooth and the neighboring tooth.

20. The non-transitory computing device readable medium of claim 18, wherein the instructions can be executed to insert a second sub-stage in the treatment plan, wherein the second sub-stage includes aligning the first tooth and neighboring tooth for IPR.

\* \* \* \* \*